(12) United States Patent
Amodt

(10) Patent No.: US 9,226,841 B1
(45) Date of Patent: Jan. 5, 2016

(54) ORTHOPEDIC FIELD SPLINT

(71) Applicant: Zachary T. Amodt, Lafayette, IN (US)

(72) Inventor: Zachary T. Amodt, Lafayette, IN (US)

( * ) Notice: Subject to any disclaimer, the term of this patent is extended or adjusted under 35 U.S.C. 154(b) by 524 days.

(21) Appl. No.: 13/672,097

(22) Filed: Nov. 8, 2012

Related U.S. Application Data

(60) Provisional application No. 61/562,555, filed on Nov. 22, 2011.

(51) Int. Cl.
*A61F 5/058* (2006.01)
*A61F 5/01* (2006.01)
*A61F 5/05* (2006.01)

(52) U.S. Cl.
CPC .............. *A61F 5/0102* (2013.01); *A61F 5/01* (2013.01); *A61F 5/05* (2013.01); *A61F 5/058* (2013.01); *A61F 5/05825* (2013.01); *A61F 5/05841* (2013.01); *A61F 5/0104* (2013.01)

(58) Field of Classification Search
CPC ........... A61F 5/00; A61F 5/01; A61F 5/0104; A61F 5/0106; A61F 5/04; A61F 5/05; A61F 5/058; A61F 5/05825; A61F 5/05841; A61F 5/0585
USPC .............................. 602/5, 12, 20, 23; 128/882
See application file for complete search history.

(56) References Cited

U.S. PATENT DOCUMENTS

| | | | | |
|---|---|---|---|---|
| 1,741,011 A | * | 12/1929 | Carvill .................. | A61F 5/0585 602/5 |
| 2,655,916 A | * | 10/1953 | Timmins ........................... | 602/4 |
| 2,753,864 A | * | 7/1956 | Weidemann, Jr. .............. | 602/23 |
| 5,947,916 A | * | 9/1999 | Riedlinger ........................ | 602/5 |
| 5,954,676 A | | 9/1999 | Kramer, III | |
| 7,621,882 B2 | * | 11/2009 | Phillips ........................... | 602/20 |

OTHER PUBLICATIONS

Vacuum Splint, described at: http://www.ambulancemodification.com/splints.html (accessed Sep. 28, 2012).
Traction Splint, described at: http://www.ambulancemodification.com/splints.html (accessed Sep. 28, 2012).
Air Splint, described at: http://www.ambulancemodification.com/splints.html (accessed Sep. 28, 2012).
SAM® splint, described at: http://sammedical.com/sam_splint.html (accessed Sep. 28, 2012).
Optimum Traction Device (O.T.D.), described at: http://www.epandr.com/products/traction/otd.php (accessed Sep. 28, 2012).
Ladder Splint described at: http://www.mlalintl.com/images/kramer_wire.jpg (accessed Sep. 28, 2012).

(Continued)

*Primary Examiner* — Alireza Nia
*Assistant Examiner* — Keri J Nelson
(74) *Attorney, Agent, or Firm* — MacMillan, Sobanski & Todd, LLC

(57) ABSTRACT

A splint includes a first substantially flexible member having an inner surface and an outer surface. A second substantially flexible member has an inner surface and an outer surface, and is hingedly attached to the first substantially flexible member. An attachment strap is slidably attached to the outer surface of the first or the second substantially flexible member, and is configured for longitudinal movement relative to the first and second substantially flexible members. A substantially rigid slat is removably mounted relative to at least one of the first and second substantially flexible members.

20 Claims, 5 Drawing Sheets

(56) References Cited

OTHER PUBLICATIONS

Military Medic Wrap Around Splint, described at: http://www.recycledgoods.com/images/s_p_11174_1.jpg (accessed Sep. 28, 2012).

Oregon Spine Splint, described at: http://www.frontmed.co.nz/Modules/ArticleList/ThumbnailOnTheFly.aspx? w=300&h=250&ImageId=765 (accessed Sep. 28, 2012).

* cited by examiner

ORTHOPEDIC FIELD SPLINT

BACKGROUND OF THE INVENTION

This invention relates in general to splints. In particular, this invention relates to an improved structure for an orthopedic splint for use in the field by military personnel, emergency medical first-responders, athletic trainers, and the like.

Many splinting devices are available for use by military personnel, athletic trainers, emergency medical first-responders and the like to splint, immobilize, and/or stabilize various orthopedic injuries.

One known splint is a vacuum splint, such as described at: http://www.ambulancemodification.com/splints.html (accessed Sep. 28, 2012). The vacuum splint includes fabric filled with small foam beads. When air is pumped out of the splint, it retains rigidity. To use the vacuum splint, the fabric is wrapped around the injured limb, and air is pumped out of the splint. The vacuum splint comes in several sizes, each designed for a specific limb. Multiple splints may need to be carried to treat different limbs. The vacuum splint has a hand pump to pump out the air in the splint. This pumping requires time the operator in the field may not have. The vacuum splint does not work if the splint is punctured. The vacuum splint may also require extended time to remove after it has been applied.

Another known splint is the traction splint, such as described at: http://www.ambulancemodification.com/splints.html (accessed Sep. 28, 2012). The traction splint is a device that may be used to immobilize a leg, while allowing traction to be applied in the event of a femur fracture. Although the traction splint may be folded in half, it is large and relatively heavy, and may be difficult for an operator can carry. The traction splint is specifically configured to splint legs. Traction is only indicated in mid-bone femur fractures, and is contraindicated for fractures tibia or fibula. Without an X-ray of the injured leg, the traction splint may be improperly applied.

A further known splint is the air splint, such a described at: http://www.ambulancemodification.com/splints.html (accessed Sep. 28, 2012). The air splint is a device that is placed over the fractured limb and inflated, in order to immobilize the limb. Each size of air splint is made for a specific limb. Although relatively light and portable, inflating the air splint is time consuming and may require more time than the operator has available. The air splint will not inflate if punctured, such as if shot, rendering the air splint non-functional. The air splint does not allow further treatment of injuries (such as bleeding), and must be completely removed if further aid is necessary. The air splint may not function properly work if bulky bandages are applied to the limb, as it may not fit over the bandages.

An additional known splint is an SAM® splint, manufactured by SAM Medical Products of Wilsonville, Oreg. and described at: http://sammedical.com/sam_splint.html (accessed Sep. 28, 2012). The SAM® splint is a long piece of aluminum covered in foam. It is malleable allowing for several shapes and angles to be formed to make splints for different areas of the body. The SAM® splint is easy to bend, but does not offer much rigidity. Due to its size, it is not useful for larger fractures such those found in the leg (other than the ankle) and is most useful for wrist and ankle injuries. This splint is useful, but only for very specific parts of the body, under very specific conditions.

Another known splint is the Optimum Traction Device (O.T.D.) manufactured by Emergency Produce and Research of Kent, Ohio and described at: http://www.epandr.com/products/traction/otd.php (accessed Sep. 28, 2012). The O.T.D. is a very small and portable device useful to apply traction to a broken femur. While small and easy to carry, the O.T.D. is not a splint. This device does not offer any immobilization of the limb. It only applies traction. It is also very difficult to place on the patient.

A further known splint is the ladder splint as shown at: http://www.mlalintl.com/images/kramer_wire.jpg (accessed Sep. 28, 2012). The ladder splint is a wire ladder that can be cut and bent to a size required to splint the fractured limb. The ladder splint is kept unbent in order to be functional when the operator, such as a medic, attempts to use it. When the ladder splint is bent before application, it can be difficult for the operator/medic to form the splint in to the correct shape. The ladder splint also has to be cut and formed which requires time that the operator/medic may not have available. Also, because the ladder splint is easy to bend, it is a less than ideal splint.

An additional splint is the military medic wrap around splint as shown at: http://www.recycledgoods.com/images/s_p_11174_1.jpg (accessed Sep. 28, 2012). The military medic wrap around splint is a splint that wraps around the limb, thereby immobilizing it. This splint comes in several pieces that may be connected together in different ways to splint several different types of fractures. This splint is relatively large and comes in a package the size of a rifle case. It is bulky, heavy, difficult to assemble, and requires a relatively long period of time to assemble and to fit on the patient.

Another splint is the Oregon spine splint as shown at: http://www.frontmed.co.nz/Modules/ArticleList/ThumbnailOnTheFly.aspx?w=300&h=250&ImageId=765 (accessed Sep. 28, 2012). The Oregon spine splint is a device that is placed on victims of vehicle accidents, so they can be safely removed from the vehicle without further spine injury. This splint is large, and its use is limited to vehicle accident victims.

Additionally, the U.S. Army is known to use a field-expedient splint. The U.S. Army's field-expedient splint is a device that military organizations, such as the Joint Special Operations Medical Training Center (JSOMTC) teaches its student to make in an austere or field environment. The field-expedient splint is typically made from tape, such as duct tape, and flat pieces of wood. The field-expedient splint is secured to the patient by cravats or whatever other material is readily available to include strips of a Soldier's uniform, rope, or tourniquets. The field-expedient splint folds and rolls to become more compact, however it takes a long time to make, making it imperfect in emergency situations. The length and width of the device varies with the Soldier who builds it.

Thus, it would be desirable to provide an improved structure for an orthopedic field splint that addresses the issues discussed above.

DETAILED DESCRIPTION OF THE INVENTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

As used in the description of the invention and the appended claims, the phrase "outer surface" is defined as the surface that will generally face away from the patient's limb that will be immobilized. The phrase "inner surface" is defined as the surface that will generally face toward the patient's limb that will be immobilized.

Figure 1:
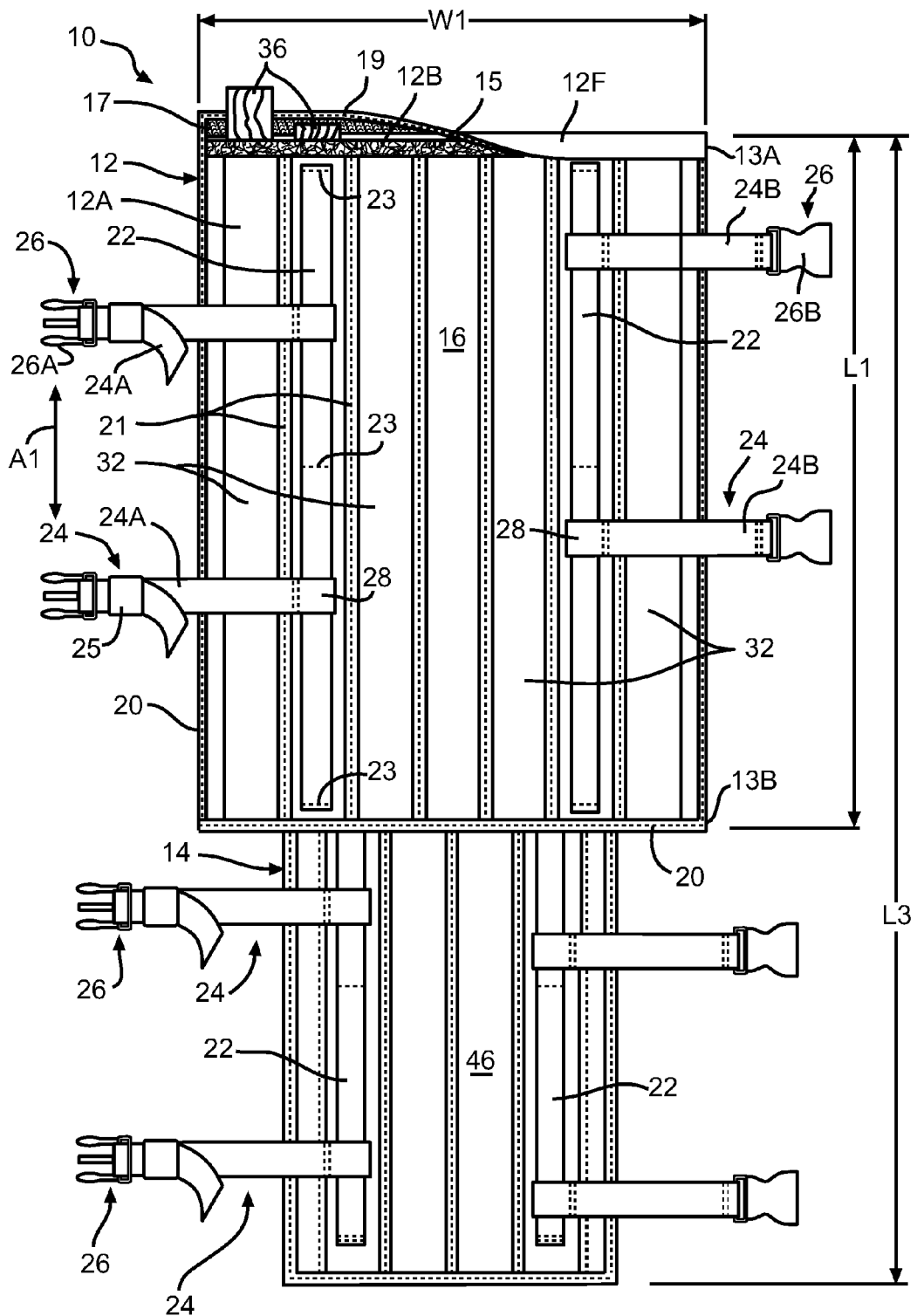
FIG. 1 is a top plan view of a first embodiment of a splint according to the invention.

Referring now to the drawings, there is illustrated in FIG. 1 a first embodiment of an orthopedic splint, indicated generally at 10, in accordance with this invention. As shown in FIG. 1, the splint 10 is in an unfolded or open position.

The illustrated splint 10 includes a first member 12 and a second member 14. The first and second members 12 and 14 are substantially rectangular and are formed from substantially flexible material such as nylon. Alternatively, the first and second members 12 and 14 may have other shapes and may be formed from other substantially flexible material or webbing, and may comprise multiple layers of fabric and/or webbing. The substantially flexible material or webbing may also be formed from other material, such as KEVLAR® fabric, GORTEX® fabric, ballistic nylon fabric, polyester and cotton blended fabric, polyester fabric, ripstop nylon fabric, and other like materials.

In the illustrated embodiment, the splint 10 is configured for use on a leg of an average size adult. The first member 12 is configured for use on the upper portion of the leg and the second member 14 (described in detail below) is configured for use on the lower portion of a leg. The illustrated first member 12 has a length L1 of about 24 inches and a width W1 of about 12 inches. Alternatively, the first member 12 may have a length L1 within the range of from about 14 inches to about 28 inches and a width W1 within the range of from about 8 inches to about 16 inches. It will be understood that the first member 12 may have dimensions smaller than described above when the intended use of the splint 10 is on a limb or portion of a limb smaller than a leg, such as an ankle, arm, or wrist or when the splint 10 will be used on a small adult or child. The first member 12 may also have dimensions larger than described above when the intended use is on a limb or portion of a limb of an adult of larger than average size or on the trunk.

Figure 2:
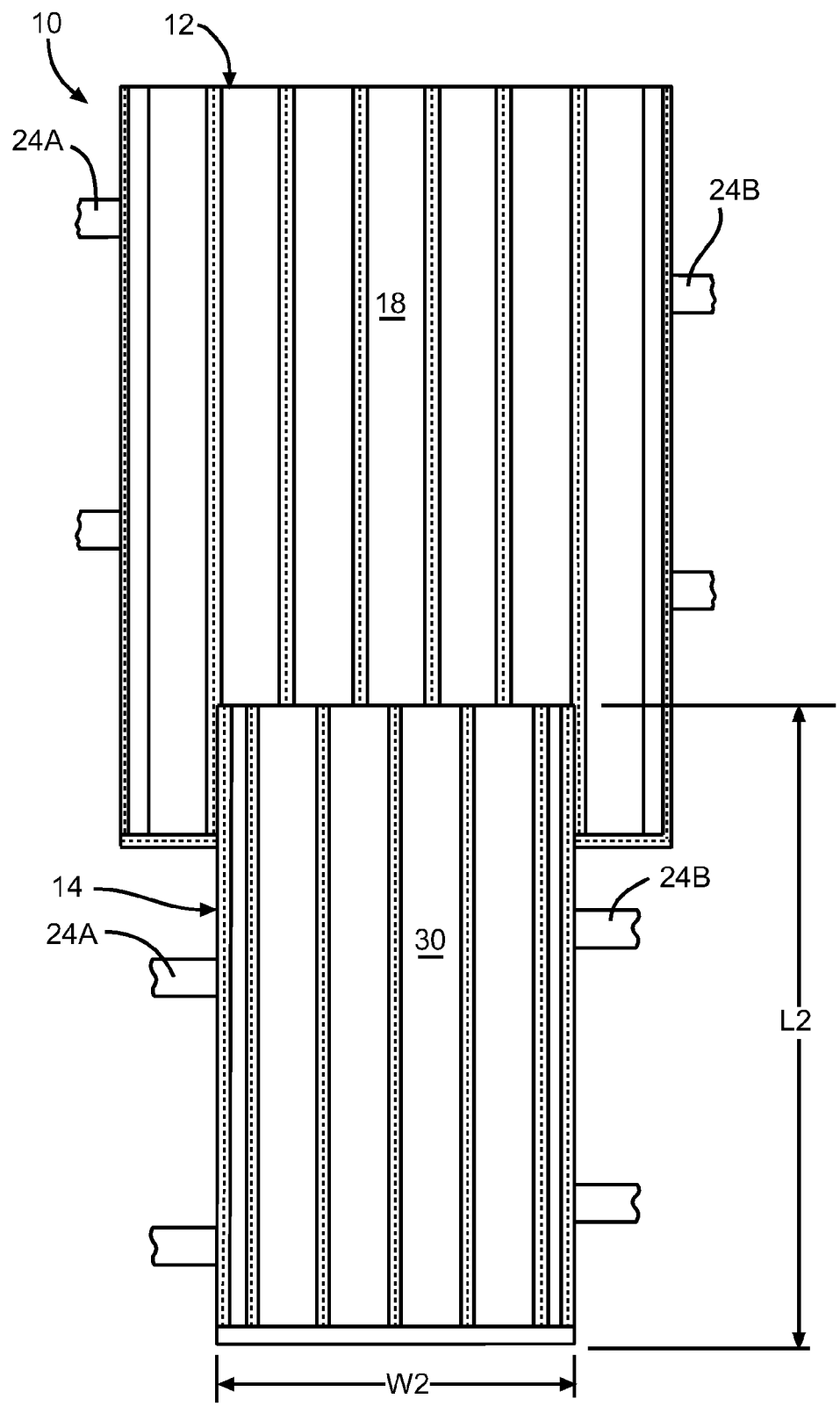
FIG. 2 is a bottom plan view of the splint illustrated in FIG. 1.

In the illustrated embodiment, the first member 12 is formed from first and second flexible fabric members 12A and 12B, respectively, attached together by a seam 20 may be sewn along the peripheral edge of the first member 12. Longitudinally extending sewn seams 21 are further sewn into the flexible fabric members 12A and 12B to further attach the flexible fabric members 12A and 12B together and to define longitudinally extending sleeves 32, described in detail below. The sleeves 32 have an open end at a first end 13A of the first member 12 and a closed end at a second end of the first member 12. The longitudinally extending sewn seams 21 further define longitudinally extending folding joints, also described in detail below. The first member 12 defines an outer surface 16 and an inner surface 18, as best shown in FIG. 2.

As shown in FIG. 1, the second flexible fabric member 12B is longer than the first flexible fabric member 12A at the first end 13A of the first member 12. The portion of the second flexible fabric member 12B that extends beyond an end of the first flexible fabric member 12A defines a closing flap 12F of the first member 12. Mechanical fastening means may be provided on one or both of the first and second flexible fabric members 12A and 12B to selectively open and close the closing flap 12F and allow access to the sleeves 32. In the illustrated embodiment, a hook and loop fastening system is illustrated and includes a loop portion 15 attached to the first flexible fabric member 12A and a hook portion 17 attached to an inside surface of the closing flap 12F. It will be understood that any other mechanical fastening means may be provided. Non-limiting examples of suitable mechanical fastening means include snaps, hooks, magnets, elastic ties, and/or buttons. If desired, a reinforcing seam 19 may be sewn along the peripheral edge of the closing flap 12F.

Although illustrated as closed by a sewn seam 20, the second end 13B of the first member 12 may also include a flap and mechanical fastening means as illustrated at the first end 13A.

A plurality of elongated mounting members 22 are attached to the outer surface 16 by any suitable means. In the illustrated embodiment, the mounting members 22 are attached by sewing, such as shown at 23. Alternatively, the mounting members 22 may be attached by other means, such as with mechanical fasteners or with adhesive. The mounting members 22 may be formed from any suitable material, including any of the materials for forming the first and second members 12 and 14 described above.

Figure 5:
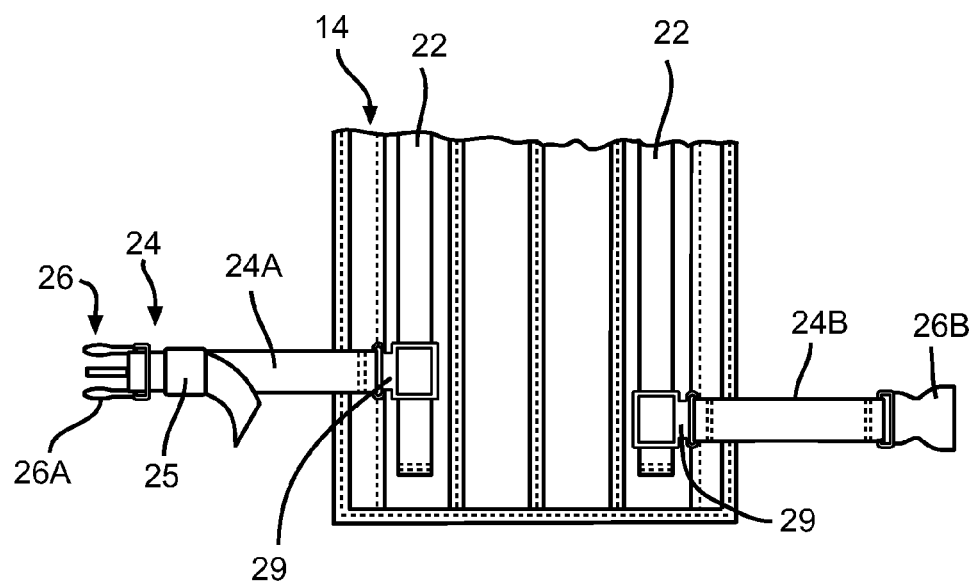
FIG. 5 is a top plan view of a portion of the splint illustrated in FIG. 1, showing an alternate embodiment of the sliding attachment member.

Pairs of adjustable attachment straps 24 are attached to the mounting members 22. The attachment straps 24 may also be formed from any suitable material, including any of the materials for forming the first and second members 12 and 14 described above. In the illustrated embodiment, a first attachment strap 24A is slidably attached to a mounting member 22 by a sliding connector 28. In the illustrated embodiment, the sliding connector 28 is formed by folding and sewing a portion of each of the first and second attachment straps 24A and 24B into a looped portion through which the mounting member 22 extends. Alternatively, as best shown in FIG. 5, a plastic or metal sliding buckle 29 may be attached to the strap 24 in lieu of the looped portion 28. The sliding connector 28 is configured to be formed at or attached to one end of the first and second attachment straps 24A and 24B and slidably attached to the mounting members 22 to allow longitudinal movement (in the direction of the arrow A1) of the first and second attachment straps 24A and 24B relative to the mounting members 22. The first attachment strap 24A includes a first buckle portion 26A of a buckle 26. A second attachment strap 24B is also attached to a mounting member 22 by a sliding connector 28. The sliding connector 28 is configured to be attached to one end of the first attachment strap 24B and slidably attached to the mounting member 22 to allow longitudinal movement (in the direction of the arrow A1) of the second attachment strap 24B relative to the mounting member 22.

The second attachment strap 24B includes a second buckle portion 26B of the buckle 26. In the illustrated embodiment, the first buckle portion 26A is adjustably attached to the first attachment strap 24A and the second attachment strap 24B is fixedly attached to the second attachment strap 24B. Alternatively, either or both of the first and second buckle portions 26A and 26B may be adjustably attached to the first and second attachment straps 24A and 24B, respectively. Further, either or both of the first and second buckle portions 26A and 26B may be fixedly attached to the first and second attachment straps 24A and 24B, respectively. Alternatively, or instead of the buckles 26, the adjustable attachment straps 24 may include other fasteners, such as hook and loop fasteners.

In the illustrated embodiment, the adjustable first attachment strap 24A includes a retaining band 25 to secure the loose free end of the first attachment strap 24A. The retaining band 25 may be formed from any suitable material such as elastic material. Alternatively, the retaining band 25 may be formed from any other suitable material, including any of the materials for forming the first and second members 12 and 14 described above.

The illustrated sleeves 32 are configured to retain slats 36. In FIG. 1, two slats 36 are shown partially extending from two sleeves 32 for illustrative purposes. Because the closing flap 12F is releasably attached to the outer surface 16 of the first member 12, the sleeves 32 may be selectively opened and closed, and the slats 36 may be removed and installed at the discretion of the user.

Figure 7:
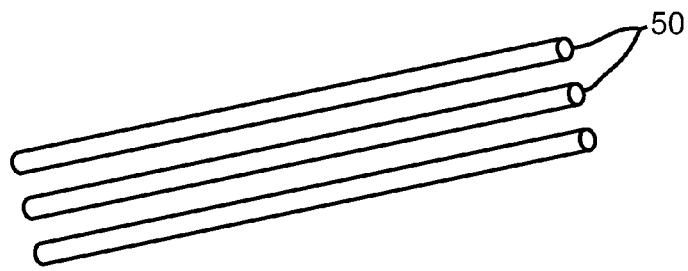
FIG. 7 is a perspective view of a plurality of rods according to the invention.

In the illustrated embodiment, the slats 36 are configured for use on a leg of an average size adult and have a length of about 18 inches and a width of about 1 inch. Alternatively, the slats 36 may have a length within the range of from about 12 inches to about 24 inches and a width within the range of from about 0.5 inches to about 3 inches. Additionally, the slats may be smaller or larger than described above depending on the intended use of the splint 10. Alternatively, in lieu of the slats 36, a plurality of rods 50, as shown in FIG. 7, may be provided. Like the slats 36, the rods 50 are configured for use on a leg of an average size adult. The rods 50 may have a length of about 18 inches and a diameter of about 0.125 inches. Alternatively, the rods 50 may have a length within the range of from about 12 inches to about 24 inches and a diameter within the range of from about 0.125 inches to about 0.5 inches.

The slats 36 and the rods 50 may be formed from any substantially rigid material. Non-limiting examples of suitable materials for use in the slats 36 and the rods 50 include wood, metal, plastic, KEVLAR®, composite materials, and combinations thereof.

The second member 14 is smaller, but substantially identical to the first member 12. The second member 14 includes an includes an outer surface 46, an inner surface 30 as shown in FIG. 2, the mounting members 22, a closing flap 14F releasably attached to the outer surface 46, and at least one pair of adjustable attachment straps 24 and their associated first and second buckle portions 26A and 26B.

The second member 14 is configured to be used in combination with the first member 12. As described above, the splint 10 is configured for use on a leg of an average size adult. The first member 12, described above, is configured for use on the upper portion of the leg and the second member 14 is configured for use on the lower portion of a leg. The illustrated second member 14 has a length L2 of about 18 inches and a width W2 of about 8 inches. Alternatively, the second member 14 may have a length L2 within the range of from about 12 inches to about 24 inches and a width W2 within the range of from about 6 inches to about 12 inches. It will be understood that the second member 14 may have dimensions smaller than described above when the intended use of the splint 10 is on a limb or portion of a limb smaller than a leg, such as an ankle, arm, or wrist or when the splint 10 will be used on a small adult or child. The second member 14 may also have dimensions larger than described above when the intended use is on a limb or portion of a limb of an adult of larger than average size or on the trunk.

When the splint 10 is in the open position as shown in FIG. 1, the splint has an overall length L3 of about 34 inches. Alternatively, the splint 10 may have an overall length L3 within the range of from about 24 inches to about 50 inches. It will be understood that the splint 10 may have dimensions smaller or larger than described above.

Figure 3:
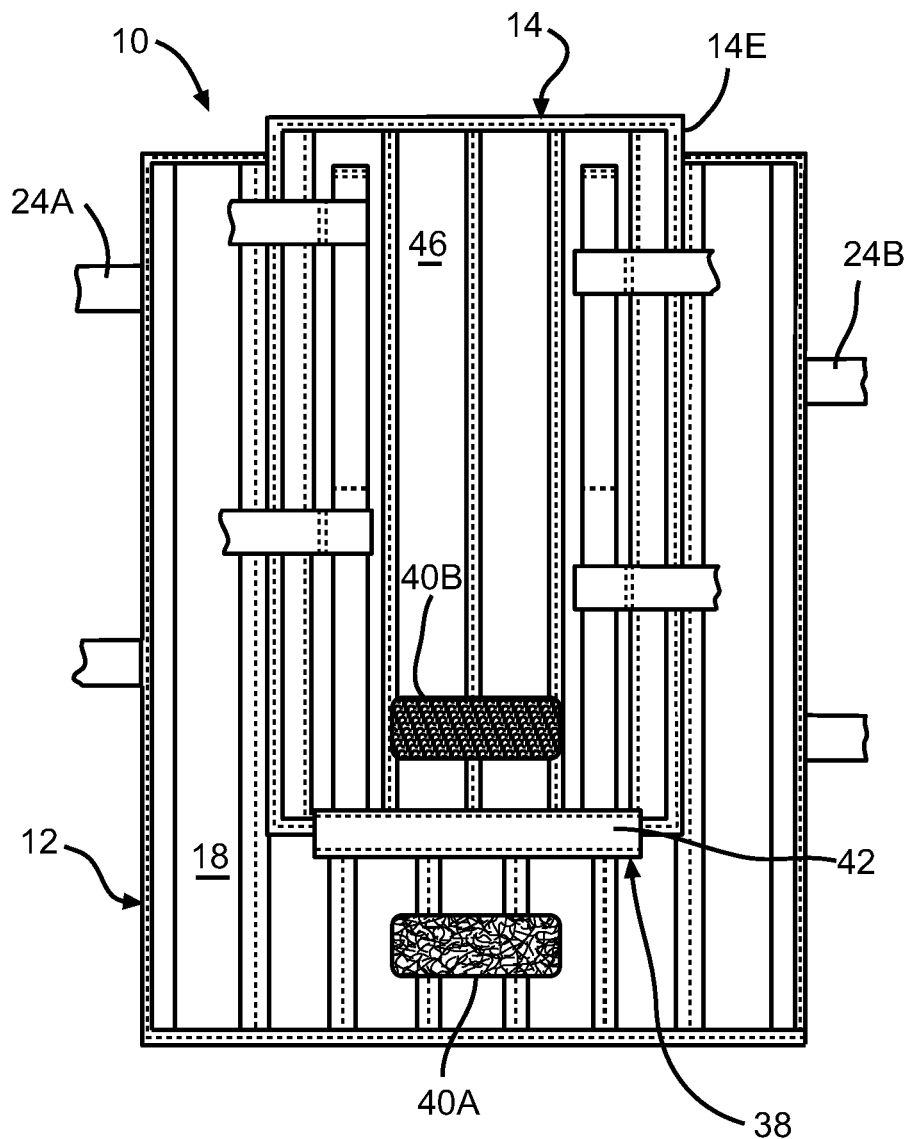
FIG. 3 is a bottom plan view of the splint illustrated in FIG. 2, showing the splint in a closed position.

Referring now to FIG. 3, the splint 10 is shown in a folded or closed position. As best shown in FIG. 3, the second member 14 is attached to the inner surface 18 of the first member 12 by a strip of fabric 38. The strip of fabric 18 may be attached to the inner surface 18 by any suitable means, such as by sewing, mechanical fasteners, or with adhesive. Alternatively, the strip of fabric 38 is not required and the second member 14 may be directly attached to the inner surface 18 of the first member 12 at a seam defined by any suitable means, such as by sewing, mechanical fasteners, or with adhesive. For example, the second member 14 may be attached to the outer surface 16 of the first member 12 at a sewn seam 48 as shown in a second embodiment of the splint 110 in FIG. 6.

If desired, complementary portions 40A and 40B of a fastener, such as a hook and loop fastener may be attached to the inner surface 18 of the first member 12 and the outer surface 46 of the second member 14, respectively. The strip of fabric 18 or the alternative seam defines a hinge 42. The purpose of the hinge 42 and fastener portions 40A and 40B will be explained below.

As shown in FIG. 3, a portion of an end 14E of the second member 14 extends beyond the first end 13A of the first member 12 when the splint 10 is in the closed position.

Figure 6:
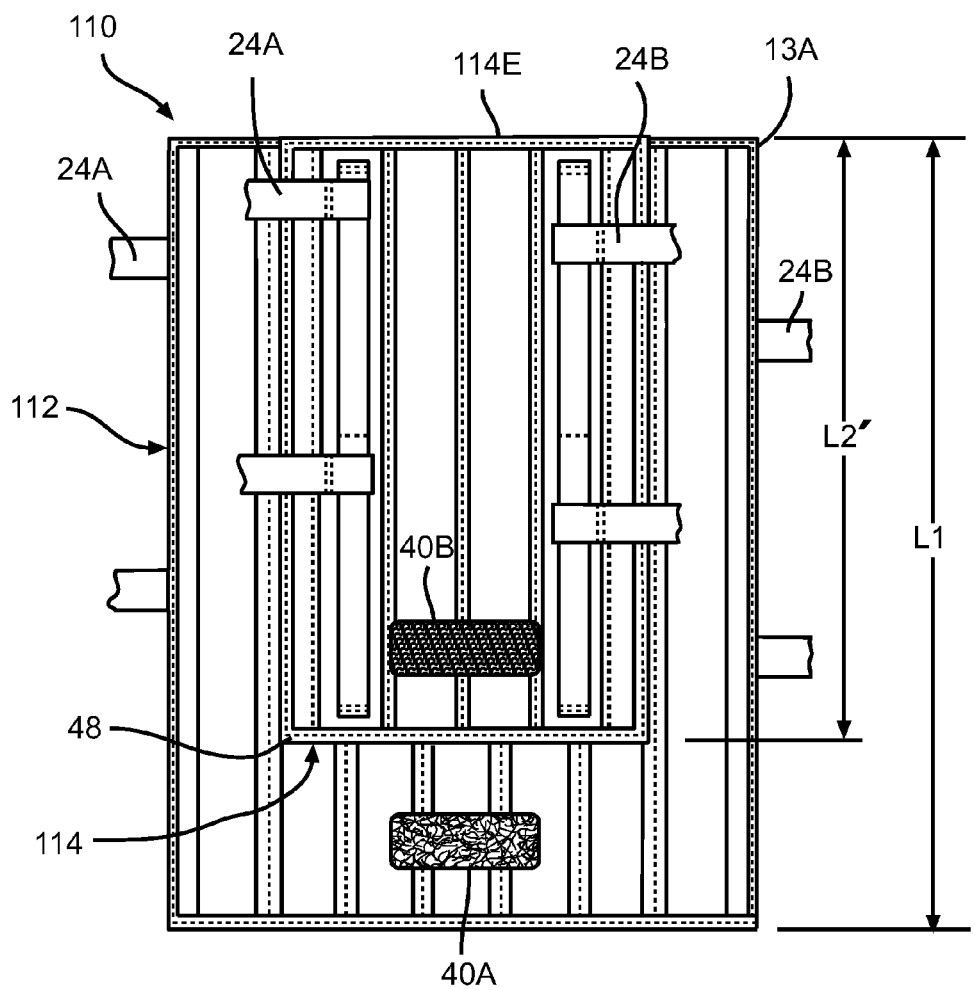
FIG. 6 is a bottom plan view of a second embodiment of the splint, showing the splint in a closed position.

Referring now to FIG. 6, a second embodiment of the orthopedic splint is indicated generally at 110. As shown in FIG. 6, the splint 110 is in the closed position. As shown in FIG. 6, the length L2' of the second member 114 may be reduced such that the end 114E of the second member 114 extends no further than the first end 13A of the first member 12 when the splint 110 is in the closed position.

As described above, FIG. 1 illustrates the splint 10 in an open position and ready to be applied to the limb of an injured person. Advantageously, the splint 10 relatively light weight and may be easily folded and rolled to a relatively small size that may be stored or carried by emergency medical personnel, such as military members who may travel long distances by foot.

Figure 4:
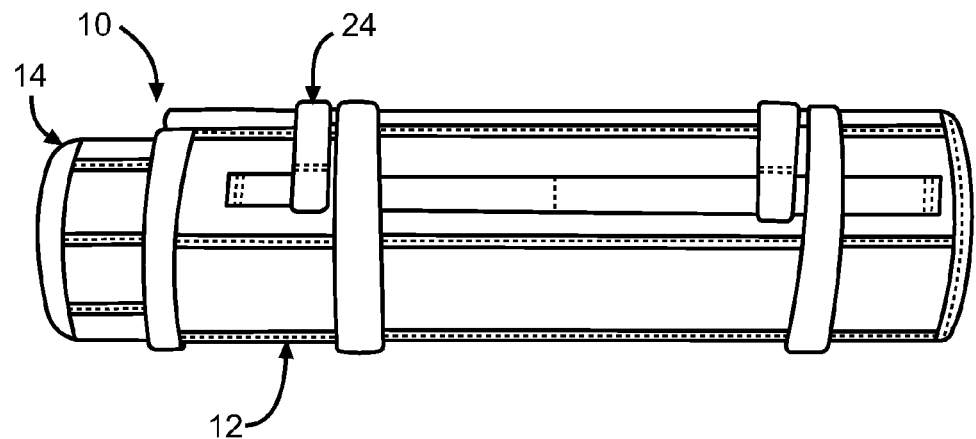
FIG. 4 is a top plan view of the splint illustrated in FIGS. 1 through 3, showing the splint in a rolled position.

To prepare the splint 10 for transport, the second member 14 is folded at the hinge 42 to bring the inner surface 30 of the second member 14 into contact with the inner surface 18 of the first member 12, as shown in FIG. 3. Once in the closed position, the splint 10 may be rolled and fastened, such as with one or more of the attachment straps 24, thus defining a rolled position as shown in FIG. 4. Alternatively, the rolled splint 10 may be stored in a flexible or rigid sleeve or outer housing (not shown).

To use the splint 10 in a field environment, the rolled splint 10, as shown in FIG. 4, may be opened or unrolled to the closed position as shown in FIG. 3. The second member 14 is then pivoted about the hinge 42 to the open position as shown in FIG. 1.

In the embodiment of the splint 10 illustrated in FIG. 3, when the second member 14 is moved from the closed position to the open position, the fastener portion 40B is moved into contact with the fastener portion 40A to assist in maintaining the splint 10 in the open position prior to the splint 10 being applied to the limb of an injured person. It will be understood that the fastener portions 40A and 40B are not required.

When the splint 10 is applied to a limb of an injured person, the operator/medic may adjust the compression applied by the splint by adjusting the tightness of the adjustable attachment straps 24. If the buckles 26 fail to fasten or if additional compression on the injured limb is required, other devices may be applied around the splint 10. Non-limiting examples of such other devices include straps with hook and loop fasteners, fabric strips, and tourniquets.

Advantageously, the material that forms the inner surface 18 of the first member 12 and the inner surface 30 of the second member 14 may be coated or impregnated with medication. Non-limiting examples of medications that may be coated or impregnated in the material of the splint 10 include, silver fiber, antibiotics, and pain mitigation medication. Additionally, tubes (not shown) of these medications may be provided within the first and/or second members 12 and 14, such as within the sleeves 32. These tubes may be configured for delivery of the medication via a bolus (not shown) or other suitable delivery device.

Another advantage of the splints of the invention is that the slats 36 may be removed from the sleeves 32 and used to splint injuries, such as injuries to the upper extremities. The removable slats 36 may also be used to splint small bone fractures and provide the "stick" for use in a conventional "sticks and rags" splint as used by military personnel.

If desired, one or more tubes (not shown) may be provided within the sleeves 32 or embedded within the material of the first and/or second members 12 and 14. These tubes may be connected to a chilled water system (not shown) after the injured limb is stabilized.

Additionally, sensors may be attached to the splint 10. For example, a pulse oximeter may be attached to the splint 10 in the region where the splint 10 will contact the patient's ankle to allow monitoring of the oxygenation of the patient's hemoglobin.

The principle and mode of operation of the splint have been described in its preferred embodiments. However, it should be noted that the splint described herein may be practiced otherwise than as specifically illustrated and described without departing from its scope.

What is claimed is:

1. A splint comprising:
    a first substantially flexible member having an inner surface and an outer surface;
    a second substantially flexible member having an inner surface and an outer surface, the second substantially flexible member hingedly attached to the first substantially flexible member, the first and second substantially flexible members having a common longitudinal axis;
    an attachment strap slidably attached to the outer surface of one of the first and second substantially flexible members, the attachment strap configured for movement parallel to the common longitudinal axis of the first and second substantially flexible members; and
    a substantially rigid slat removably mounted relative to at least one of the first and second substantially flexible members.

2. The splint according to claim 1, wherein the splint is configured for movement between a closed position wherein the second substantially flexible member is folded against the first substantially flexible member such that the inner surface of the second substantially flexible member engages the inner surface of the first substantially flexible member, and an open position wherein the second substantially flexible member is folded away from the first substantially flexible member such that the inner surface of the second substantially flexible member and the inner surface of the first substantially flexible member face the same direction.

3. The splint according to claim 2, wherein the splint is further configured for movement to a rolled position defining a rolled splint, such that in the rolled position a longitudinal axis of the rolled splint is substantially parallel with a longitudinal axis of the slat.

4. The splint according to claim 1, wherein one of the first and second substantially flexible members includes a longitudinally extending sleeve.

5. The splint according to claim 4, wherein the substantially rigid slat is removably mounted in the sleeve.

6. The splint according to claim 5, wherein the substantially rigid slat is formed from one of wood, metal, plastic, and composite material.

7. The splint according to claim 1, wherein one of the first and second substantially flexible members includes a plurality of longitudinally extending sleeves.

8. The splint according to claim 7, further including a plurality of the substantially rigid slats, one of which is removably mounted in each sleeve.

9. The splint according to claim 7, further including longitudinally extending seams sewn into the one of the first and second substantially flexible members, the seams defining the longitudinally extending sleeves.

10. The splint according to claim 9, wherein the longitudinally extending sewn seams further define longitudinally extending folding joints.

11. The splint according to claim 1, wherein the length of the attachment strap is adjustable.

12. The splint according to claim 11, wherein the attachment strap comprises a pair of attachment straps, each attachment strap of the pair slidably attached to the outer surface of the one of the first and second substantially flexible members.

13. The splint according to claim 1, wherein a plurality of attachment straps are slidably attached to the outer surface of one of the first and second substantially flexible members.

14. The splint according to claim 1, wherein the inner surfaces of the first and second flexible members are configured to be placed against a patient's limb.

15. The splint according to claim 1, further including medication which is one of embedded in and coated on the inner surface of one of the first and second substantially flexible members.

16. A splint comprising:
   a substantially flexible member defining a longitudinal axis;
   a sleeve formed in the substantially flexible member and extending parallel to the longitudinal axis of the substantially flexible member;
   a substantially rigid slat removably mounted in the sleeve;
   a mounting member attached to the sleeve; and
   an attachment strap slidably attached to the mounting member, the attachment strap configured for movement along the longitudinal axis of the substantially flexible member.

17. The splint according to claim 16, wherein the substantially flexible member includes a plurality of longitudinally extending sleeves.

18. The splint according to claim 17, further including a substantially rigid slat removably mounted in each sleeve.

19. The splint according to claim 18, further including longitudinally extending seams sewn into the substantially flexible member, the seams defining the longitudinally extending sleeves.

20. A splint comprising:
   a first substantially flexible member having an inner surface and an outer surface;
   a second substantially flexible member having an inner surface and an outer surface, the second substantially flexible member hingedly attached to the first substantially flexible member;
   a first substantially rigid slat removably mounted within the first substantially flexible member; and
   a second substantially rigid slat removably mounted within the second substantially flexible member;
   wherein the splint is configured for movement between a closed position wherein the second substantially flexible member is folded against the first substantially flexible member perpendicular to a longitudinal axis of the first and second slats such that the inner surface of the second substantially flexible member engages the inner surface of the first substantially flexible member, and an open position wherein the second substantially flexible member is folded away from the first substantially flexible member such that the inner surface of the second substantially flexible member and the inner surface of the first substantially flexible member face the same direction; and
   wherein the splint is movable between the closed and open positions with the first substantially rigid slat mounted within the first substantially flexible member and the second substantially rigid slat mounted within the second substantially flexible member.

* * * * *